United States Patent
Yang

[11] Patent Number: 6,001,612
[45] Date of Patent: Dec. 14, 1999

[54] HETERODUPLEX PCR CLONING

[76] Inventor: Robert Che-An Yang, 8th Fl., 152 Jen-Ai Rd., Yun-Ho City, Taipei 100, Taiwan

[21] Appl. No.: 09/265,654

[22] Filed: Mar. 10, 1999

[30] Foreign Application Priority Data

Nov. 6, 1998 [TW] Taiwan .................................. 87118466

[51] Int. Cl.⁶ .............................. C12Q 1/68; C12P 19/34; C12N 15/00; C07H 21/04
[52] U.S. Cl. .......................... 435/91.2; 435/6; 435/320.1; 536/24.33
[58] Field of Search ........................... 435/91.2, 6, 320.1; 536/24.33

[56] References Cited

PUBLICATIONS

Liu, "Hetero–stagger Cloning: Efficient and Rapid Cloning of PCR Products", Nucleic Acids Research 24:2458–2459, 1996.

Holton et al., "A Simple and Efficient Method for Direct Cloning of PCR Products Using ddT–tailed Vectors", Nucleic Acids Research 19:1156, 1990.

Marchuk et al., "Construction of T–vectors, a Rapid and General System for Direct Cloning of Unmodified PCR Products", Nucleic Acids Research 19:1154, 1990.

Shuldiner et al., "PCR–induced (Ligase–free) Subcloning: A Rapid Reliable Method to Subclone Polymerase Chain Reaction (PCR) Products", Nucleic Acids Research 18:1920, 1990.

*Primary Examiner*—Ardin H. Marschel
*Assistant Examiner*—Joyce Tung
*Attorney, Agent, or Firm*—Fish & Richardson P.C.

[57] ABSTRACT

The invention relates to a method of cloning a target nucleic acid sequence by performing two PCR reactions to generate two PCR products differing in terminal sequences. The PCR products thus obtained are denatured and annealed together to form a heteroduplex, which is ready for ligation and transformation of bacteria without any restriction digestion.

16 Claims, 1 Drawing Sheet

HETERODUPLEX PCR CLONING

BACKGROUND OF THE INVENTION

The polymerase chain reaction (PCR) permits rapid amplification of a nucleic acid having an intervening nucleic acid sequence flanked by known sequences. In PCR, the known sequence information is used to design single-stranded primers which will hybridize to the nucleic acid. After annealing, the primers are extended by a polymerase. The extended products are then removed from the nucleic acid so that a new cycle of annealing and extension can be performed. In performing successive cycles of annealing and extension, the nucleic acid is thereby amplified.

PCR also allows easy cloning of any nucleic acid sequence flanked by known sequences by designing primers which contain restriction endonuclease cleavage sequences. After amplification, the double-stranded PCR product can be digested with the corresponding endonucleases to obtain small 5' or 3' overhang sequences characteristic of the endonucleases. The PCR products are ready for cloning into a vector digested with the same endonucleases. However, this method is limited by the often inefficient cleavage of restriction endonuclease cleavage sites near an end of a double-stranded nucleic acid.

SUMMARY OF THE INVENTION

The invention is based on the discovery of a highly efficient method of cloning a nucleic acid sequence into a double-stranded DNA vector. The method includes performing two separate PCR reactions to produce two similar double-stranded DNA products, each having a terminal sequence that is identical to an overhang produced by a restriction endonuclease. Alternatively, one of the PCR products contains two terminal overhang sequences, while the other PCR product contains no overhang sequences. The two DNA products are then heated and annealed to form a heteroduplex species that can be ligated to an appropriately digested DNA vector.

Accordingly, the invention features a method of ligating a hybrid nucleic acid product into a double-stranded DNA vector by amplifying, by a first polymerase chain reaction, a double-stranded DNA to form a first nucleic acid product, the first polymerase chain reaction employing (1) a first primer including (i) a 5' terminal sequence identical to, or exactly complementary to, an overhang sequence produced by a first restriction endonuclease and (ii) a priming sequence of a first strand of the double-stranded DNA, and (2) a second primer including a priming sequence of a second strand of the double-stranded DNA, the priming sequence of the second strand being 5' to a sequence of the second strand which is exactly complementary to the priming sequence of the first strand. Consequently, the first nucleic acid product contains, in sequential order, (a) the 5' terminal sequence of the first primer, (b) the priming sequence of the first strand, (c) a sequence of the double-stranded DNA between the priming sequence of the first strand and the priming sequence of the second strand, and (d) the priming sequence of the second strand.

This method also includes amplifying, by a second polymerase chain reaction, the double-stranded DNA to form a second nucleic acid product, the second polymerase chain reaction employing (1) a third primer including (i) a 5' terminal sequence identical to, or exactly complementary to, an overhang sequence produced by a second restriction endonuclease and (ii) the priming sequence of the second strand, and (2) a fourth primer comprising the priming sequence of the first strand. Consequently, the second nucleic acid product contains, in sequential order, (a) the priming sequence of the first strand, (b) the sequence of the double-stranded DNA between the priming sequence of the first strand and the priming sequence of the second strand, (c) the priming sequence of the second strand, and (d) the 5' terminal sequence of the third primer.

To form the heteroduplex, the first nucleic acid product and the second nucleic acid product are denatured, then annealed together in a mixture to form a hybrid nucleic acid product. This hybrid nucleic acid product is also included in the invention.

Of course, since the restriction sites can be chosen so that the hybrid nucleic acid product contains both 5' overhangs, 3' overhangs, or both, the invention also features a method of ligating a hybrid nucleic acid product into a double-stranded DNA vector amplifying, by a first polymerase chain reaction, a double-stranded DNA to form a first nucleic acid product, the first polymerase chain reaction employing (1) a first primer including (i) a 5' terminal sequence identical to, or exactly complementary to, an overhang sequence produced by a first restriction endonuclease and (ii) a priming sequence of a first strand of the double-stranded DNA, and (2) a second primer comprising (i) a 5' terminal sequence identical to, or exactly complementary to, an overhang sequence produced by a second restriction endonuclease and (ii) a priming sequence of a second strand of the double-stranded DNA, the priming sequence of the second strand being 5' to a sequence of the second strand which is exactly complementary to the priming sequence of the first strand. Consequently, the first nucleic acid product contains, in sequential order, (a) the 5' terminal sequence of the first primer, (b) the priming sequence of the first strand, (c) a sequence of the doublestranded DNA between the priming sequence of the first strand and the priming sequence of the second strand, (d) the priming sequence of the second strand, and (e) the 5' terminal sequence of the second primer.

This variant method also includes amplifying, by a second polymerase chain reaction, the double-stranded DNA to form a second nucleic acid product, the second polymerase chain reaction employing (1) a third primer including the priming sequence of the second strand, and (2) a fourth primer comprising the priming sequence of the first strand. Consequently, the second nucleic acid product contains in sequential order (a) the priming sequence of the first strand, (b) the sequence of the double-stranded DNA between the priming sequence of the first strand and the priming sequence of the second strand, and (c) the priming sequence of the second strand.

To clone the hybrid nucleic acid product, the hybrid nucleic acid product is ligated to a double-stranded DNA vector that has been digested with the first restriction endonuclease and the second restriction endonuclease. Finally, it is noted that the overhang sequence produced by the first restriction endonuclease is different from the overhang sequence produced by the second restriction endonuclease.

The methods of the invention can include one or more of the following. The priming sequence of the first strand and the 5' terminal sequence identical to, or exactly complementary to, the overhang sequence produced by the first restriction endonuclease are adjacent in the first primer. The priming sequence of the second strand and the 5' terminal sequence identical to, or exactly complementary to, the overhang sequence produced by the second restriction endonuclease are adjacent in the third primer.

The methods of the invention are useful in efficiently and directionally cloning a wide variety of DNA fragments into circular, double-stranded DNA vectors via user-chosen restriction sites. These methods eliminate the need for restriction endonuclease digestion of the ends of PCR products, an often inefficient step in these products. Consequently, when compared to known cloning techniques, the methods result in unexpectedly superior cloning efficiencies (see below).

Other features or advantages of the present invention will be apparent from the following drawings and detailed description, and also from the claims.

DETAILED DESCRIPTION OF THE INVENTION

Figure 1:
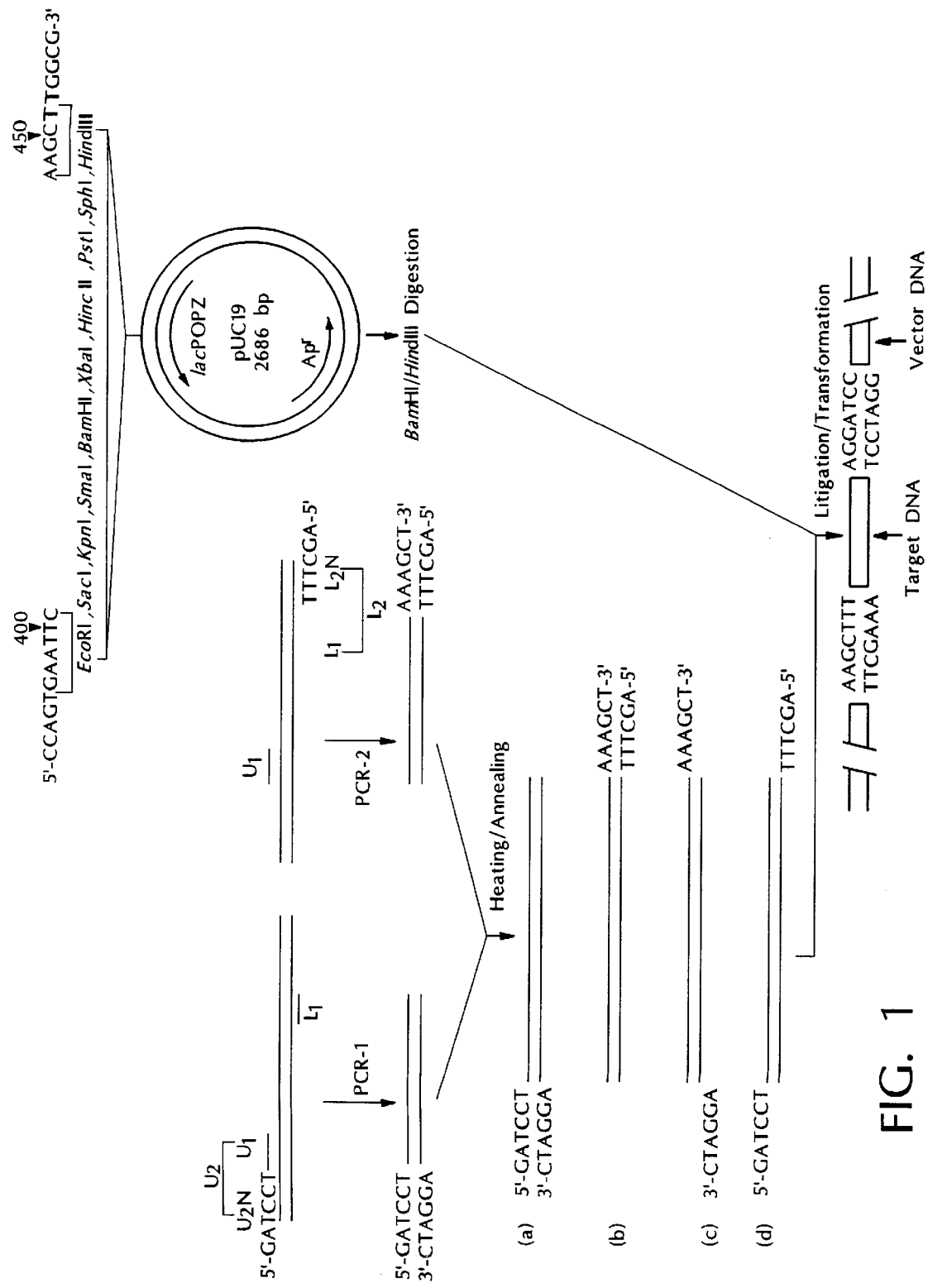
FIG. 1 is a schematic representation of a method of the invention.

The invention relates to the development of a new highly efficient PCR-based cloning method. Contemplated within the scope of the claims are any PCR cloning method that includes the generation of two PCR products and forming, by mixing, heating, and annealing the two PCR products together, a heteroduplex having terminal restriction endonuclease overhang sequences. The heteroduplex is then ligated to a linearized DNA vector having terminal restriction endonuclease overhang sequences which are complementary to the overhang sequences in the heteroduplex. General procedures for PCR can be found in Innis et al., PCR Protocols: A guide to Methods and Applications, Academic Press, Inc., San Diego, Calif., 1990.

Without further elaboration, it is believed that one skilled in the art can, based on the above disclosure and the description below, utilize the present invention to its fullest extent. The following example is to be construed as merely illustrative of how one skilled in the art can practice the invention and are not limitative of the remainder of the disclosure in any way. Any publications cited in this disclosure are hereby incorporated by reference.

Cloning HPV Sequences from Patient DNA Samples

Human Papilloma Virus-16 (HPV-16) sequences from patient cell samples were cloned via PCR into various standard vectors as follows.

The primers used for PCR were U1 (CCAGGCCCATTTTGTAGCTTCAACC; SEQ ID NO:1), L1 (CCTAACAGCGGTATGTAAGGCGTTG; SEQ ID NO:2), U2 (GATCCTCCAGGCCCATTTTGTAGCTTCAACC; SEQ ID NO:3), and L2 (AGCTTTCCTAACAGCGGTATGTAAGGCGTTG; SEQ ID NO:4). U1 and U2 share the same priming sequence except that U2 has an additional short sequence of 4 to 6 nucleotides (designated U2N) at the 5' end, thereby creating a BamH I overhang sequence at the terminus of any PCR product produced using the U2 primer. Similarly, L1 and L2 share the same priming sequence, except that L2 has an extra short stretch of 4 to 6 bases (designated L2N) at the 5' end, thereby creating a Hind III restriction site at the terminus of any PCR product produced using the L2 primer. Both BamH I and Hind III produce 5' overhangs. In addition, to account for the deoxyadenosine known to be added to the 3' end of PCR products derived from Taq polymerase, primers U2 and L2 contain an extra deoxythymidine between the priming sequence and the overhang sequence. A schematic of the primer design is shown in FIG. 1.

Generally, it was recognized that the optimal length for U2N and L2N be formulated between 'n+r' and 'n+r+1', inclusive, where 'n' denotes the number of overhanging nucleotides for the selected restriction endonuclease, 'r' denotes remainder base(s). Though both formulas are applicable, the 'n+r' formula is logically sufficient for PCR products which are derived from using a DNA polymerase, such as Pwo or Pfu that does not add any extra base to the 3' terminus of the PCR products. As mentioned above, the terminal sequences, U2N and L2N, require an extra deoxythymidine to account for the addition of deoxyadenosine by Taq polymerase, a very widely used thermophilic DNA polymerase to date. The latter situation thus requires that 'n+r+1' formula for designing a terminal sequence. For example, Hind III specifies a recognition sequence of 5'-AAGCTT. On cleavage it produces 5'-AGCTT with an overhang of 'AGCT' (N=4) at the 5' terminus and a remainder base of a single 'T' (r=1). But in order to complement with the Taq-derived extra 'A' at the 3' terminus of the PCR product, another 'T' residue is required. I therefore use the 'n+r+1' formula to design the 5' terminal sequence as 5'-AGCTTT. PCR products cloned with restriction sequences using either design formula are retrievable with the selected restriction enzymes.

The target for amplification was genomic DNA isolated from cervical cytobrush samples of patients infected with HPV-16. Genomic DNA was isolated by standard methods as described in Sambrook et al., Molecular Cloning, A Laboratory Manual, 2nd ed., Cold Spring Harbor Laboratory Press, New York, N.Y., pp 1.62–1.67, 1989; and Karlsen et al., J Clin Micrbiol 34:2095–2100, 1996.

Referring back to FIG. 1, genomic DNA derived from each patient was used in two separate PCRs. In one PCR (PCR-1), primers U2 and L1 were employed to generate a double-stranded PCR product having a 5' terminal sequence including the BamH I overhang sequence GATC. In the other PCR (PCR-2), primers U1 and L2 were employed to generate a PCR product having a 5' terminal sequence including the Hind III overhang sequence AGCT.

PCR reactions were carried out in a total volume of 50 $\mu$l containing 20 pmol (0.165 $\mu$g) of each primer, 5 $\mu$g of genomic DNA, 2.5 U of Taq polymerase (Gibco-BRL), 0.25 mM each of dNTPs, 20 mM Tris-HCl (pH 8.4), 10 mM KCl, and 1.5 mM MgCl2. The PCR mixture was overlaid with a 50 $\mu$l drop of mineral oil. Amplification was achieved after 40 cycles of denaturation at 94° C., annealing at 64° C., and polymerization at 72° C. Each segment of the cycle was one minute in length. Temperature cycling was performed on a Perkin Elmer Cetus thermocycler.

The PCR products were isolated from the reactions by electrophoresis on a 2% high melting point agarose gel (SeaKem). The expected 273 base pair and 285 base pair PCR products were purified using the High Pure Purification Kit (Boehringer Mannheim) according to manufacturer's instructions. Purity of the isolated PCR products was confirmed by fractionation on a 2% high melting point agarose gel.

0.45 $\mu$g of each isolated PCR product were mixed in a total volume of 30 $\mu$l of TE buffer (10 mM Tris [pH 7.6] and 1 mM EDTA), and the mixture was covered with 50 $\mu$l of mineral oil. The mixture was heated to 95° C. for 5 minutes and allowed to cool gradually to room temperature.

As shown in FIG. 1, four species of fragments were formed after annealing. Species (a) and (b) represent the original fragments produced from PCR-1 and PCR-2. Species (c) is a heteroduplex containing 3' overhangs, which are incompatible with a vector digested with BamH I and Hind III. Species (d) is a heteroduplex containing 5' overhang sequences which can be ligated to a vector linearized with BamH I and Hind III.

Plasmid pUC19 (Gibco-BRL) was digested with BamH I and Hind III. This vector was ligated to the annealed mixture in a 15 µl reaction containing 150 ng of insert DNA, 50 mM Tris-HCl (pH 7.8), 10 mM MgCl2, 10 mM dithiothreitol, 1 mM ATP, 50 µg/ml BSA, 50 ng of vector DNA, 5 U of T4 polynucleotide kinase (New England Biolabs), and 2 U of T4 ligase (New England Biolabs). The ligation reaction was first incubated at 37° C. for 15 minutes to phosphorylate the 5' hydroxyl of the insert DNA, then incubated at 14° C. overnight to maximize ligation. Although a single-base gap was formed between the overhang sequences of the hybrid DNA and the vector sequences in the ligated DNA, this gap was expected to be filled-in and repaired upon introduction into bacteria.

Forty microliters of competent DH5α E. coli (Gibco-BRL) cells were mixed with 1 µl of the completed ligation reaction. Calcium-facilitated transformation was carried out using the standard methods described in Sambrook et al., supra. Transformation of uncut pUC19 was routinely performed to ensure consistent competence for each transformation. 50 to 100 µl from a 250 µl transformation mix were spread on a 2×YT agar plate (16 g tryptone, 10 g yeast extract, 5 g NaCl, and 20 g agar per liter) containing 100 µg/ml ampicillin, 40 µg/ml 5-bromo-4-chloro-3-indolyl-β-D-galactopyranoside (X-gal), and 40 µg/ml isopropyl-β-D-thiogalactoside (IPTG). The plates were incubated overnight at 37° C. Transformants were visually screened for inserts by observing the presence of white colonies. Blue colonies were considered false transformants. The ligation yielded, on average, over 2000 white colonies and about 170 blue colonies per microgram of DNA used for the transformation.

To determine whether the white colonies contained the correct insert, colony hybridizations were carried out as described in Sambrook et al., supra. A total of 60 to 80 transformants were selected for analysis. Masterplates were prepared by stabbing the selected colonies with toothpicks and inoculating a region of fresh 2×YT plates covered with an appropriately sized nitrocellulose membrane. After overnight incubation at 37° C., the bacteria on the filters were lysed and the DNA denatured in 0.5 N NaOH. The filters were then neutralized in 0.5 M Tris-HCl, pH 8.0, and washed twice in 6×SSC. After baking for 2 hours at 80° C. under vacuum, the filters were prehybridized in 5×Denhardt's solution (0.1% (w/v) ficoll, 0.1% (w/v) polyvinylpyrrolidone, 0.1% BSA, and 100 µg/ml sheared, denatured salmon sperm DNA) containing 25% (v/v) formamide at 37° C. for about 30 minutes. The filters were then hybridized with HPV-16-specific $^{32}$P-labeled probe (GTTTCCTGCTTGCCATGCGTGCCAAATCCC; SEQ ID NO:5) at 37° C. overnight. After washing with 0.2×SSC containing 0.1% SDS, the filters were visualized by autoradiography using BioMax-MS film (Kodak). The percentage of white colonies containing the correct insert was determined to be about 98%. To determine the number of false negatives, blue colonies were subjected to colony hybridization as described immediately above. An average of 3% of the blue colonies contained HPV-16 sequence and were considered false negative.

Although the heteroduplex PCR method described above produced a high yield of transformants, it would have been useful to compare this method to other standard methods, such as the TA cloning method or the restriction cutback method.

The TA cloning method takes advantage of the propensity of Taq polymerase to add an additional deoxyadenosine to the 3' end of the PCR product (Mead et al., Bio/Technology 9:657–663, 1991; and Holton et al., Nucl Acids Res 19:1156, 1990). The Taq-amplified PCR products can then be ligated to a vector containing 3' deoxythymidine overhangs.

The restriction cutback method involves designing PCR primers which contain restriction endonuclease sites, thereby producing a double-stranded PCR product having user-chosen restriction sites near the ends of the PCR product. The PCR product is then digested with the chosen restriction endonucleases in preparation for ligation to a vector. As discussed above, the cloning efficiency of the restriction cutback method is often reduced because of inefficient digestion of the PCR product ends by the restriction endonucleases.

Here, the PCR products generated above did not contain the full BamH I sequence GGATCC, nor the full Hind III sequence AAGCTT. Instead, a single terminal base pair was missing from each restriction site sequence (see primers U2 and L2 above). However, in a separate experiment, it was determined that these "partial" restriction site sequences at an end of a double-stranded PCR product can serve almost as efficiently as the full restriction site sequence. The cutting efficiency of the full BamH I sequence at the terminus of a double-stranded PCR products was measured to be about 15%, comparable to the 12% cutting efficiency of the partial sequence in primer U2. Similarly, the cutting efficiency of the full Hind III sequence at the terminus of a double-stranded PCR product was measured to be about 70%, comparable to the 68.4% cutting efficiency for the partial sequence in primer L2.

The efficiency of the heteroduplex PCR cloning method was compared to that of the TA cloning method and the restriction cutback method, with the results shown in Table 1.

TABLE 1

| | | Colony Count According to Patient DNA Sample | | | | |
| --- | --- | --- | --- | --- | --- | --- |
| Cloning Method | Measurement | XP-1 | XP-2 | XP-3 | XP-4 | XP-5 |
| Heteroduplex | Transformation: | $1.9 \times 10^6$ | $7.5 \times 10^5$ | $1.9 \times 10^6$ | $1.1 \times 10^6$ | $1.7 \times 10^6$ |
| | Total: | 2398 | 474 | 2439 | 699 | 1050 |
| | White: | 2230 (98%) | 417 (88%) | 2244 (92%) | 653 (93%) | 993 (95%) |
| | White with Insert: | 2185 (95%) | 417 (100%) | 2154 (96%) | 646 (99%) | 993 (100%) |
| | Blue: | 168 (7%) | 57 (12%) | 195 (8%) | 46 (7%) | 57 (5%) |
| | Blue with Insert: | N/A | 0 (0%) | 0 (0%) | 3 (6%) | 3 (5%) |

TABLE 1-continued

| Cloning Method | Measurement | Colony Count According to Patient DNA Sample | | | | |
| --- | --- | --- | --- | --- | --- | --- |
| | | XP-1 | XP-2 | XP-3 | XP-4 | XP-5 |
| TA | Net Positive: | 2230 (91%) | 417 (88%) | 2154 (88%) | 649 (99%) | 996 (95%) |
| | Transformation: | $8.1 \times 10^5$ | $1.7 \times 10^5$ | $6.8 \times 10^5$ | $1.6 \times 10^5$ | $2.3 \times 10^5$ |
| | Total: | 1450 | 111 | 904 | 103 | 164 |
| | White: | 283 (20%) | 22 (20%) | 74 (8%) | 31 (30%) | 18 (11%) |
| | White with Insert: | 243 (86%) | 22 (100%) | 66 (89%) | 31 (100%) | 17 (94%) |
| | Blue: | 1167 (81%) | 89 (80%) | 830 (92%) | 72 (70%) | 146 (89%) |
| | Blue with Insert: | N/A | 36 (40%) | 166 (20%) | 30 (42%) | 51 (35%) |
| | Net Positive: | 243 (17%) | 58 (52%) | 232 (26%) | 62 (60%) | 68 (41%) |
| Restriction Cutback | Transformation: | $7.8 \times 10^5$ | $2.1 \times 10^5$ | $2.2 \times 10^5$ | $1.4 \times 10^5$ | $2.4 \times 10^5$ |
| | Total: | 1003 | 135 | 283 | 91 | 159 |
| | White: | 421 (42%) | 75 (56%) | 93 (33%) | 27 (30%) | 56 (35%) |
| | White with Insert: | 232 (55%) | 27 (36%) | 28 (30%) | 14 (52%) | 15 (25%) |
| | Blue: | 582 (58%) | 60 (44%) | 190 (67%) | 64 (70%) | 103 (65%) |
| | Blue with Insert: | N/A | 0 (0%) | 0 (0%) | 0 (0%) | 0 (0%) |
| | Net Positive: | 232 (23%) | 27 (27%) | 28 (10%) | 14 (15%) | 14 (9%) |

Each of the values presented in Table 1 was the average of two values obtained from separate experiments. The "transformation" count was expressed in colony forming units per microgram of DNA. The "total" count was the number of colony forming units per 100 $\mu$l of competent bacteria plated. The "white" count was the number of white colonies followed by, in parenthesis, the percentage of white colonies among the "total" count. The number of "white with insert" colonies was confirmed as true positives as described above, with the percentage of white colonies in parentheses. The values for "blue" and "blue with insert" (false negatives) were obtained as described for "white" and "white with insert." The "net positive" count represents the number of true positives as confirmed by the presence of the insert, with the percentage of "total" in parentheses.

The data in Table 1 indicated that the heteroduplex cloning method was surprisingly superior to both the TA or restriction cutback methods. For examples, the number of false positives for the restriction cutback method was significantly greater than that for the heteroduplex method. In addition, the number of false negatives for the TA cloning method were far higher than for the heteroduplex method.

Other Embodiments

It is to be understood that while the invention has been described in conjunction with he detailed description thereof, the foregoing description is intended to illustrate and not limit the scope of the invention, which is defined by the scope of the appended claims. Other aspects, advantages, and modifications are within the scope of this invention.

For example, the method of the invention can be performed using asymmetric PCR, whereby the individual strands of the heteroduplex to be ligated are obtained by arithmetic amplification of a target nucleic acid.

What is claimed is:

1. A method of ligating a hybrid nucleic acid product into a double-stranded DNA vector, the method comprising
amplifying, by a first polymerase chain reaction, a double-stranded DNA to form a first nucleic acid product, the first polymerase chain reaction employing (1) a first primer comprising (i) a 5' terminal sequence identical to, or exactly complementary to, an overhang sequence produced by a first restriction endonuclease and (ii) a priming sequence of a first strand of the double-stranded DNA, and (2) a second primer comprising a priming sequence of a second strand of the double-stranded DNA, the priming sequence of the second strand being 5' to a sequence of the second strand which is exactly complementary to the priming sequence of the first strand, whereby the first nucleic acid product comprises, in sequential order, (a) the 5' terminal sequence of the first primer, (b) the priming sequence of the first strand, (c) a sequence of the double-stranded DNA between the priming sequence of the first strand and the priming sequence of the second strand, and (d) the priming sequence of the second strand;
amplifying, by a second polymerase chain reaction, the double-stranded DNA to form a second nucleic acid product, the second polymerase chain reaction employing (1) a third primer comprising (i) a 5' terminal sequence identical to, or exactly complementary to, an overhang sequence produced by a second restriction endonuclease and (ii) the priming sequence of the second strand, and (2) a fourth primer comprising the priming sequence of the first strand, whereby the second nucleic acid product comprises, in sequential order, (a) the priming sequence of the first strand, (b) the sequence of the double-stranded DNA between the priming sequence of the first strand and the priming sequence of the second strand, (c) the priming sequence of the second strand, and (d) the 5' terminal sequence of the third primer;
denaturing the first nucleic acid product and the second nucleic acid product;
annealing the denatured first nucleic acid product and the denatured second nucleic acid product together to form a hybrid nucleic acid product; and
ligating the hybrid nucleic acid product to a double-stranded DNA vector that has been digested with the first restriction endonuclease and the second restriction endonuclease,
wherein the overhang sequence produced by the first restriction endonuclease is different from the overhang sequence produced by the second restriction endonuclease.

2. The method of claim 1, wherein the priming sequence of the first strand and the 5' terminal sequence identical to, or exactly complementary to, the overhang sequence produced by the first restriction endonuclease are adjacent in the first primer.

3. The method of claim 2, wherein the priming sequence of the second strand and the 5' terminal sequence identical to, or exactly complementary to, the overhang sequence produced by the second restriction endonuclease are adjacent in the third primer.

4. The method of claim 1, wherein the priming sequence of the second strand and the 5' terminal sequence identical to, or exactly complementary to, the overhang sequence produced by the second restriction endonuclease are adjacent in the third primer.

5. A method of forming a hybrid nucleic acid product, the method comprising
amplifying, by a first polymerase chain reaction, a double-stranded DNA to form a first nucleic acid product, the first polymerase chain reaction employing (1) a first primer comprising (i) a 5' terminal sequence identical to, or exactly complementary to, an overhang sequence produced by a first restriction endonuclease and (ii) a priming sequence of a first strand of the double-stranded DNA, and (2) a second primer comprising a priming sequence of a second strand of the double-stranded DNA, the priming sequence of the second strand being 5' to a sequence of the second strand which is exactly complementary to the priming sequence of the first strand, whereby the first nucleic acid product comprises, in sequential order, (a) the 5' terminal sequence of the first primer, (b) the priming sequence of the first strand, (c) a sequence of the double-stranded DNA between the priming sequence of the first strand and the priming sequence of the second strand, and (d) the priming sequence of the second strand;
amplifying, by a second polymerase chain reaction, the double-stranded DNA to form a second nucleic acid product, the second polymerase chain reaction employing (1) a third primer comprising (i) a 5' terminal sequence identical to, or exactly complementary to, an overhang sequence produced by a second restriction endonuclease and (ii) the priming sequence of the second strand, and (2) a fourth primer comprising the priming sequence of the first strand, whereby the second nucleic acid product comprises, in sequential order, (a) the priming sequence of the first strand, (b) the sequence of the double-stranded DNA between the priming sequence of the first strand and the priming sequence of the second strand, (c) the priming sequence of the second strand, and (d) the 5' terminal sequence of the third primer;

denaturing the first nucleic acid product and the second nucleic acid product; and annealing the denatured first nucleic acid product and the denatured second nucleic acid product together to form a hybrid nucleic acid product, wherein the overhang sequence produced by the first restriction endonuclease is different from the overhang sequence produced by the second restriction endonuclease.

6. The method of claim 5, wherein the priming sequence of the first strand and the 5' terminal sequence identical to, or exactly complementary to, the overhang sequence produced by the first restriction endonuclease are adjacent in the first primer.

7. The method of claim 6, wherein the priming sequence of the second strand and the 5' terminal sequence identical to, or exactly complementary to, the overhang sequence produced by the second restriction endonuclease are adjacent in the third primer.

8. The method of claim 5, wherein the priming sequence of the second strand and the 5' terminal sequence identical to, or exactly complementary to, the overhang sequence produced by the second restriction endonuclease are adjacent in the third primer.

9. A method of ligating a hybrid nucleic acid product into a double-stranded DNA vector, the method comprising amplifying, by a first polymerase chain reaction, a double-stranded DNA to form a first nucleic acid product, the first polymerase chain reaction employing (1) a first primer comprising (i) a 5' terminal sequence identical to, or exactly complementary to, an overhang sequence produced by a first restriction endonuclease and (ii) a priming sequence of a first strand of the double-stranded DNA, and (2) a second primer comprising (i) a 5' terminal sequence identical to, or exactly complementary to, an overhang sequence produced by a second restriction endonuclease and (ii) a priming sequence of a second strand of the double-stranded DNA, the priming sequence of the second strand being 5' to a sequence of the second strand which is exactly complementary to the priming sequence of the first strand, whereby the first nucleic acid product comprises, in sequential order, (a) the 5' terminal sequence of the first primer, (b) the priming sequence of the first strand, (c) a sequence of the double-stranded DNA between the priming sequence of the first strand and the priming sequence of the second strand, (d) the priming sequence of the second strand, and (e) the 5' terminal sequence of the second primer;

amplifying, by a second polymerase chain reaction, the double-stranded DNA to form a second nucleic acid product, the second polymerase chain reaction employing (1) a third primer comprising the priming sequence of the second strand, and (2) a fourth primer comprising the priming sequence of the first strand, whereby the second nucleic acid product comprises in sequential order (a) the priming sequence of the first strand, (b) the sequence of the double-stranded DNA between the priming sequence of the first strand and the priming sequence of the second strand, and (c) the priming sequence of the second strand;

denaturing the first nucleic acid product and the second nucleic acid product;

annealing the denatured first nucleic acid product and the denatured second nucleic acid product together to form a hybrid nucleic acid product; and ligating the hybrid nucleic acid product to a double-stranded DNA vector that has been digested with the first restriction endonuclease and the second restriction endonuclease, wherein the overhang sequence produced by the first restriction endonuclease is different from the overhang sequence produced by the second restriction endonuclease.

10. The method of claim 9, wherein the priming sequence of the first strand and the 5' terminal sequence identical to, or exactly complementary to, the overhang sequence produced by the first restriction endonuclease are adjacent in the first primer.

11. The method of claim 10, wherein the priming sequence of the second strand and the 5' terminal sequence identical to, or exactly complementary to, the overhang sequence produced by the second restriction endonuclease are adjacent in the third primer.

12. The method of claim 9, wherein the priming sequence of the second strand and the 5' terminal sequence identical to, or exactly complementary to, the overhang sequence produced by the second restriction endonuclease are adjacent in the third primer.

13. A method of forming a hybrid nucleic acid product, the method comprising amplifying, by a first polymerase chain reaction, a double-stranded DNA to form a first nucleic acid product, the first polymerase chain reaction employing (1) a first primer comprising (i) a 5' terminal sequence identical to, or exactly complementary to, an overhang sequence produced by a first restriction endonuclease and (ii) a priming sequence of a first strand of the double-stranded DNA, and (2) a second primer comprising (i) a 5' terminal sequence identical to, or exactly complementary to, an overhang sequence produced by a second restriction endonuclease and (ii) a priming sequence of a second strand of the double-stranded DNA, the priming sequence of the second strand being 5' to a sequence of the second strand which is exactly complementary to the priming sequence of the first strand, whereby the first nucleic acid product comprises, in sequential order, (a) the 5' terminal sequence of the first primer, (b) the priming sequence of the first strand, (c) a sequence of the double-stranded DNA between the priming sequence of the first strand and the priming sequence of the second strand, (d) the priming sequence of the second strand, and (e) the 5' terminal sequence of the second primer;

amplifying, by a second polymerase chain reaction, the double-stranded DNA to form a second nucleic acid product, the second polymerase chain reaction employing (1) a third primer comprising the priming sequence of the second strand, and (2) a fourth primer comprising the priming sequence of the first strand, whereby the second nucleic acid product comprises in sequential order (a) the priming sequence of the first strand, (b) the sequence of the double-stranded DNA between the priming sequence of the first strand and the priming sequence of the second strand, and (c) the priming sequence of the second strand;

denaturing the first nucleic acid product and the second nucleic acid product; and annealing the denatured first nucleic acid product and the denatured second nucleic acid product together to form a hybrid nucleic acid product, wherein the overhang sequence produced by the first restriction endonuclease is different from the overhang sequence produced by the second restriction endonuclease.

14. The method of claim 13, wherein the priming sequence of the first strand and the 5' terminal sequence identical to, or exactly complementary to, the overhang sequence produced by the first restriction endonuclease are adjacent in the first primer.

15. The method of claim 14, wherein the priming sequence of the second strand and the 5' terminal sequence identical to, or exactly complementary to, the overhang sequence produced by the second restriction endonuclease are adjacent in the third primer.

16. The method of claim 13, wherein the priming sequence of the second strand and the 5' terminal sequence identical to, or exactly complementary to, the overhang sequence produced by the second restriction endonuclease are adjacent in the third primer.

* * * * *

SEQUENCE LISTING

<160> NUMBER OF SEQ ID NOS: 5

<210> SEQ ID NO 1
<211> LENGTH: 25
<212> TYPE: DNA
<213> ORGANISM: Human papilloma virus

<400> SEQUENCE: 1
ccaggcccat tttgtagctt caacc                                         25

<210> SEQ ID NO 2
<211> LENGTH: 25
<212> TYPE: DNA
<213> ORGANISM: Human papilloma virus

<400> SEQUENCE: 2
cctaacagcg gtatgtaagg cgttg                                         25

<210> SEQ ID NO 3
<211> LENGTH: 31
<212> TYPE: DNA
<213> ORGANISM: Human papilloma virus

<400> SEQUENCE: 3

```
gatcctccag gcccattttg tagcttcaac c                                              31

<210> SEQ ID NO 4
<211> LENGTH: 31
<212> TYPE: DNA
<213> ORGANISM: Human papilloma virus

<400> SEQUENCE: 4
agctttccta acagcggtat gtaaggcgtt g                                              31

<210> SEQ ID NO 5
<211> LENGTH: 30
<212> TYPE: DNA
<213> ORGANISM: Human papilloma virus

<400> SEQUENCE: 5
gtttcctgct tgccatgcgt gccaaatccc                                                30
```